(12) United States Patent
Kang

(10) Patent No.: US 11,583,428 B2
(45) Date of Patent: Feb. 21, 2023

(54) SCOLIOSIS BRACE AND MANUFACTURING METHOD THEREFOR

(71) Applicant: Standing Tall Co., Ltd., Seongnam-si (KR)

(72) Inventor: Sun Young Kang, Seongnam-si (KR)

(73) Assignee: Standing Tall Co., Ltd., Seongnam-si (KR)

( * ) Notice: Subject to any disclaimer, the term of this patent is extended or adjusted under 35 U.S.C. 154(b) by 977 days.

(21) Appl. No.: 16/304,279

(22) PCT Filed: Dec. 13, 2016

(86) PCT No.: PCT/KR2016/014588
§ 371 (c)(1),
(2) Date: Sep. 3, 2019

(87) PCT Pub. No.: WO2017/204429
PCT Pub. Date: Nov. 30, 2017

(65) Prior Publication Data
US 2019/0388261 A1    Dec. 26, 2019

(30) Foreign Application Priority Data

May 26, 2016  (KR) .................. 10-2016-0064832

(51) Int. Cl.
*A61F 5/02* (2006.01)
*A61F 5/03* (2006.01)
*A61F 5/01* (2006.01)

(52) U.S. Cl.
CPC .............. *A61F 5/024* (2013.01); *A61F 5/026* (2013.01); *A61F 5/03* (2013.01); *A61F 2005/0158* (2013.01); *A61F 2005/0167* (2013.01); *A61F 2005/0197* (2013.01)

(58) Field of Classification Search
CPC .. A61F 5/024; A61F 5/026; A61F 5/03; A61F 2005/0158; A61F 2005/0167; A61F 2005/0197; A61F 5/02; A61F 13/14; A61F 13/148; A61F 5/01
See application file for complete search history.

(56) References Cited

U.S. PATENT DOCUMENTS

| 4,202,327 | A | * | 5/1980 | Glancy | ................... | A61F 5/022 |
| | | | | | | 602/19 |
| 4,658,807 | A | * | 4/1987 | Swain | .................. | A47C 31/126 |
| | | | | | | 602/19 |
| 5,360,392 | A | | 11/1994 | McCoy | | |

(Continued)

OTHER PUBLICATIONS

International Search Report dated Mar. 15, 2017.

*Primary Examiner* — Tarla R Patel
(74) *Attorney, Agent, or Firm* — LEEPI

(57) ABSTRACT

The present invention relates to a scoliosis brace worn on the body so as to enable the normal curvature of the spine to be restored, and a manufacturing method therefor. The scoliosis brace according to one embodiment of the present invention comprises: a support part worn so as to cover one shoulder or one side of the abdominal region of the body; and a pressure band coupled so as to connect one side and the other side of the support part, and covering one side or the other side of the abdominal region of the body or one side or the other side of the chest region of the body, with respect to the support part, so as to pressurize and support the same.

14 Claims, 11 Drawing Sheets

(56) References Cited

U.S. PATENT DOCUMENTS

| | | | | |
|---|---|---|---|---|
| 5,449,338 A | * | 9/1995 | Trudell | A61F 5/024 602/5 |
| 5,599,286 A | * | 2/1997 | Labelle | A61F 5/024 602/5 |
| 7,967,767 B2 | * | 6/2011 | Ogilvie | A61F 5/024 602/5 |
| 8,066,653 B2 | * | 11/2011 | Seon | A61F 5/0123 602/5 |
| 10,265,210 B2 | * | 4/2019 | Perez | A61F 5/026 |
| 2007/0010768 A1 | * | 1/2007 | Simanovsky | A61F 5/026 602/5 |
| 2014/0330187 A1 | * | 11/2014 | Perez | A61F 5/028 602/19 |

\* cited by examiner

SCOLIOSIS BRACE AND MANUFACTURING METHOD THEREFOR

TECHNICAL FIELD

The present invention relates to a scoliosis brace and a manufacturing method therefor that is worn on the body so as to enable the normal curvature of the spine to be restored.

DESCRIPTION OF THE RELATED ART

In general, scoliosis is a condition in which the spine curves to the side and is rotated and deformed, as illustrated in FIG. 1. If the spine curves to the side at angles ranging from 20° to 40°, a brace worn to pressurize the side is used to treat the curved spine instead of a surgery as illustrated as the arrow in FIG. 1.

Conventional scoliosis braces (e.g. Milwaukee brace, Boston brace. TLSO brace) consist of solid plastics.

Most of the braces are shaped like a container. The container-shaped braces cover the entire chest region. Thus, a user cannot even pick up an object on the floor. In this case, the user has breathing difficulties, feels bloated after a meal and experiences other difficulties.

To treat the curved spine, a brace has to be worn for almost 24 hours. Thus, even in the winter, users often have sweat rashes. In particular, adolescents who have to wear such a brace for 24 hours may experience mental problems such as depression.

Even though such a brace is worn for a long time, it is hard to correct spine curvature completely because braces consist of solid plastics. Such a brace pressurizes a curved portion of the spine with the same intensity. In the early step of wearing the brace, the brace seems effective in treating the curved spine. However, when the brace is worn for a long period of time, the brace functions only as a supporter.

As a means to solve the above-described problems, a band-type brace continues to pressurize a curved portion of the spine with an elastic band. Thus, the band-type brace is more effective in reducing the degree of curvature of the spine than conventional braces. However, such a brace causes discomfort to users in their daily lives because the band-type brace is configured to cover regions ranging from the shoulder to the thigh. For instance, a band is crossed four times from the shoulder to the back and fixed with two buttons provided at the bottom region and two buttons provided at a region between the belly button and the reproductive organ. Thus, whenever users go to the bathroom, they have to repeat tying and untying the band. Additionally, they cannot wear tight clothing including tops and bottoms because the band is fixed up to the thigh region and feel uncomfortable when they walk. As described above, users have to commit a large amount of time and effort to wearing the band-type brace. Thus, they are unwilling to wear such braces for 24 hours.

In addition, conventionally, a cast is made for an individual in accordance with the shape of a curved portion of the body, and a base plate having the same shape as the curved portion is manufactured with the cast. It takes much time and it costs a lot to make a cast, and casts differ in quality depending on the manufacturer's experience.

Further, when a brace is replaced with a new one due to the damage of the brace, a case has to be re-made. Thus, a user has to re-visit a store that sells braces or a brace manufacturer again. After a cast is made at the store, the case may be damaged in the process of transferring the cast to a manufacturer. As a result, a flawed brace may be manufactured.

DETAILED DESCRIPTION OF THE INVENTION

Technical Problems

As a means to solve the above-described problems, the present invention is directed to providing a scoliosis brace and a manufacturing method therefor that is easily worn and taken off.

Additionally, the present is directed to providing a scoliosis brace and a manufacturing method therefor that is capable of adjusting the intensity of pressure according to the degree of curvature of the spine or a body region.

Further, the present is directed to providing a manufacturing method for a scoliosis brace, which includes inputting body measurements of a user and manufacturing a base plate through 3D printing, thereby making it possible to save time and costs for manufacturing a scoliosis brace and remotely manufacturing a scoliosis brace.

Technical Solutions

As a means to achieve the above-described purposes, provided is a scoliosis brace including a support part covering one side of the abdominal region of the body so as to support the same; and a pressure band consisting of an elastic material, coupled to one side and the other side of the support part so as to connect the same, and covering the other side of the abdominal region of the body so as to pressurize and support the same.

According to a preferred feature of the present invention, the length of the pressure band is adjustable and the pressure band may include a pair of coupling members provided on one side thereof.

According to another preferred feature of the present invention, the support part may include a first support plate covering one side of the abdominal region of the body so as to support the same, and a second support plate spaced apart from the lower portion of the first support plate and covering one side of the abdominal region, one side of the waist region, or one side of the pelvis region of the body so as to support the same.

According to another preferred feature of the present invention, the support part may include a first support plate configured to extend so as to be hung on one shoulder of the body, and a second support plate spaced apart from the lower portion of the first support plate and covering one side of the abdominal region, one side of the waist region, or one side of the pelvis region of the body so as to support the same.

According to another preferred feature of the present invention, the support part may include a first support plate configured to extend so as to be hung on one shoulder of the body, and a second support plate spaced apart from the lower portion of the first support plate and covering the other side of the abdominal region, the other side of the waist region, or the other side of the pelvis region of the body so as to support the same.

According to another preferred feature of the present invention, the second support plate may include an extension part curved and extended downward and outward from both ends of the second support plate, and an expansion part the width of which is expanded and which is formed at the end of the extension part.

According to another preferred feature of the present invention, the support part may further include a connecting member whose upper end is coupled to one end of the first support plate and whose lower end is coupled to one end of the second support plate, and a spine support member whose upper end is coupled to the other end of the first support plate, whose lower end is coupled to the other end of the second support plate and which supports the spine region of the body.

According to another preferred feature of the present invention, the support part may further include a first coupling hole formed at the connecting member and coupled to one end of the pressure ban, and a second coupling hole formed at the spine support member and coupled to the other end of the pressure band.

According to another preferred feature of the present invention, the support part may further include a loop member protruding downward from one side of the second support plate, and a fixing band penetrating the loop member and covering the thigh region of the body.

According to another preferred feature of the present invention, the support part may include a base plate consisting of a soft material and having a shape corresponding to a curved shape of the surface of the body, and a reinforcement plate consisting of a synthetic resin and coupled to the outer side of the base plate.

According to another preferred feature of the present invention, the support part may further include a shock absorbing member consisting of an elastic member and coupled to the inner side of the base plate.

According to another preferred feature of the present invention, the support part may further include a cover plate consisting of a metallic material and coupled to the outer side of the reinforcement plate.

According to another preferred feature of the present invention, the base plate may include a plurality of parts that are divisionally printed out through 3D printing.

According to yet another preferred feature of the present invention, the reinforcement plate may be integrally formed through laser cutting.

Additionally, as a means to achieve the above-described purposes, provided is a manufacturing method for a scoliosis brace, including (a) taking measurements of a user's body and inputting the measurements; (b) performing 3D modeling on the basis of the measurements input; (c) 3D-printing a base plate according to a shape of the 3D model; (d) piling a reinforcement plate on the outer surface of the base plate; and (e) adding a shock absorbing member on the inner surface of the base plate.

In this case, according to a preferred feature of the present invention, the manufacturing method for a scoliosis brace may further include (f) coupling a cover plate to the outer surface of the reinforcement plate.

According to another preferred feature of the present invention, the (c) step may include printing out a plurality of parts through 3D printing divisionally.

According to yet another preferred feature of the present invention, the (d) step may include laser-cutting the reinforcement plate consisting of a synthetic resin integrally.

Advantageous Effects

A scoliosis brace according to the present invention can improve scoliosis by means of an elastic pressure band that is coupled to one side of a support part and pressurizes a curved portion of the spine.

Additionally, a scoliosis brace according to the present invention is easily worn with a detachable band and does not cause discomfort to a user during physical activities.

Additionally, a scoliosis brace according to the present invention can significantly relieve pain and correct a curved spine in the case of c-shaped scoliosis which is the most common type of scoliosis.

Further, a manufacturing method for a scoliosis brace according to the present invention is effective in remote manufacturing and saving manufacturing time because a brace is manufactured by means of 3D printing on the basis of 3D modeling.

BRIEF DESCRIPTION OF THE INVENTION

BEST MODE FOR CARRYING OT THE INVENTION

Figure 1:
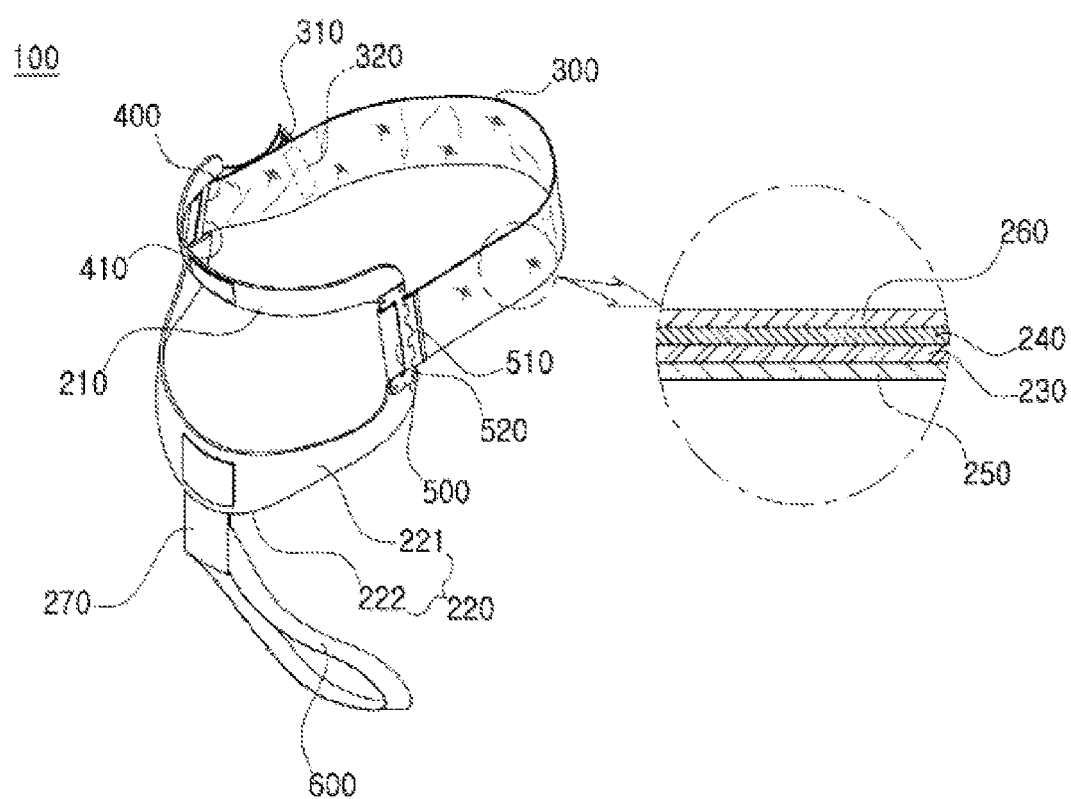
FIG. 1 is a perspective view of a scoliosis brace according to the first embodiment of the present invention.

Embodiments of the present invention will be described in detail with reference to the attached drawings. However, the embodiments are provided only to help one of ordinary skill in the art to which the present invention pertains to easily understand and carry out the present invention. Thus, it should be understood that the protection scope of the present invention is not limited to the embodiments. Additionally, throughout this specification, like reference numerals denote components with identical technical features.

Embodiment

Figure 2:
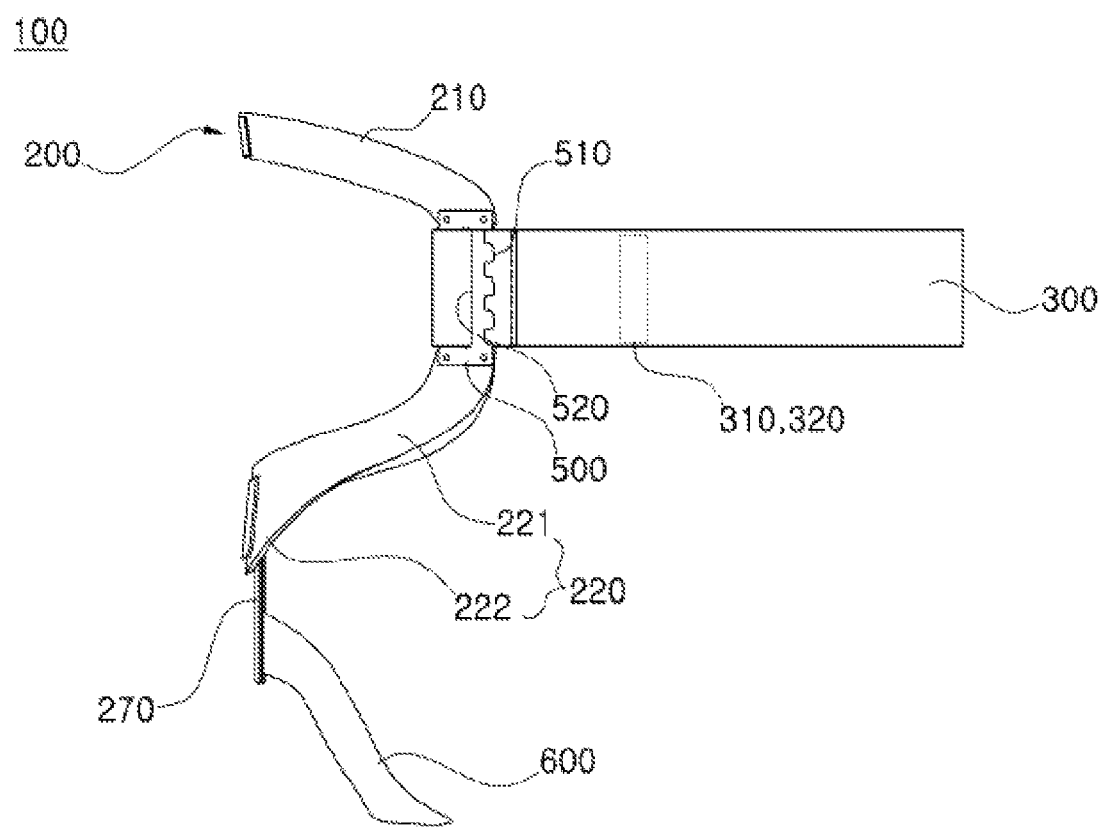
FIG. 2 is a front view of a scoliosis brace according to the first embodiment of the present invention.
Figure 3:
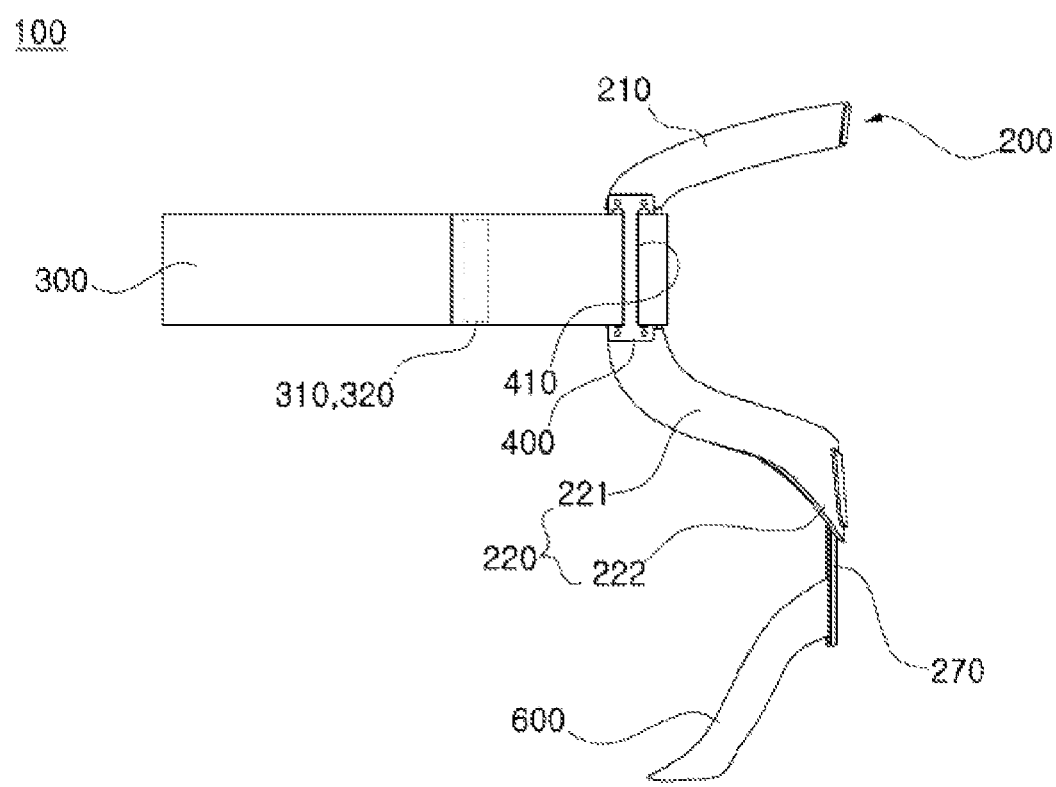
FIG. 3 is a rear view of a scoliosis brace according to the first embodiment of the present invention.
Figure 4:
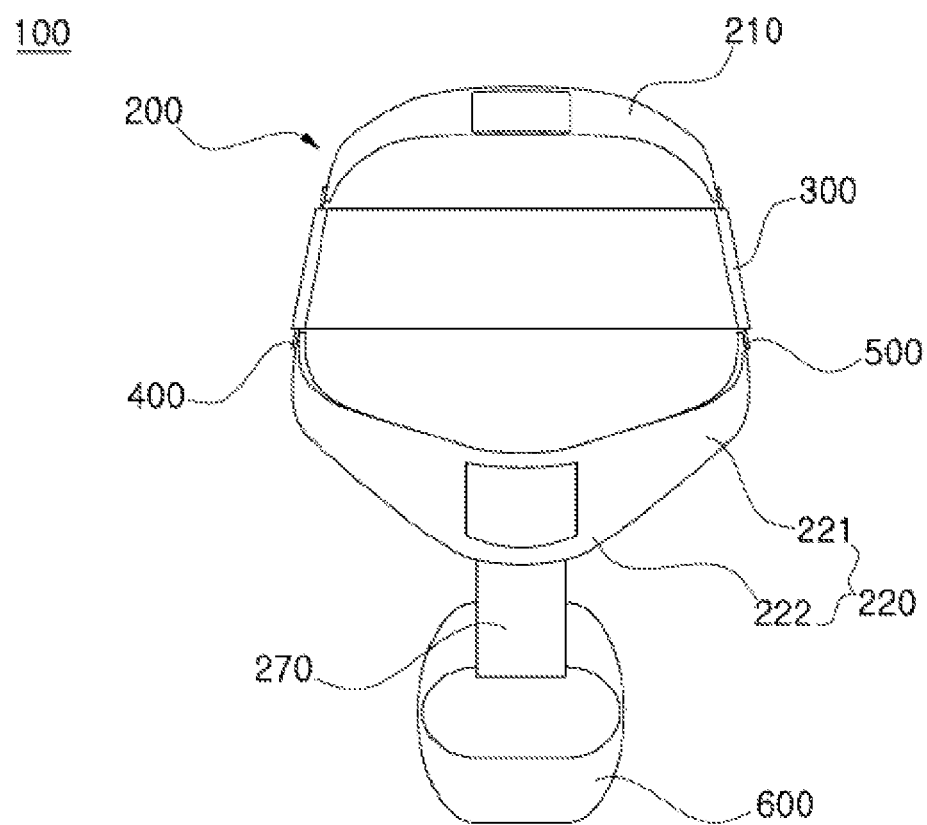
FIG. 4 is a side view of a scoliosis brace according to the first embodiment of the present invention.

FIG. 1 is a perspective view of a scoliosis brace according to the first embodiment of the present invention, FIG. 2 is a front view of a scoliosis brace according to the first embodiment of the present invention, FIG. 3 is a rear view of a scoliosis brace according to the first embodiment of the present invention, and FIG. 4 is a side view of a scoliosis brace according to the first embodiment of the present invention.

A scoliosis brace 100 (herein after referred to as "brace") according to the first embodiment of the present invention, as illustrated in FIGS. 1 to 4, includes a support part 200 covering one side of the abdominal region of the body so as to support the same, and a pressure band 300 covering the other side of the abdominal region of the body so as to pressurize and support the same on the opposite side of the support part 200. In this case, the pressure band 300 faces the support part 200 and is coupled to one side and the other side of the support part so as to connect the same.

The support part 200 includes a first support plate 210 and a second support plate 220 spaced apart from the first plate at the lower portion of the same. The first support plate 210 has the shape of a belt with a predetermined width and length, and covers and supports one side of the abdominal region of the body. For instance, when the brace 100 is worn, the first support plate 210 may go past the center of the abdominal region and then go under the armpit or the chest and may extend to the center of the back region, and the inner surface of the brace comes into close contact with the surface of the body.

The second support plate 220 covers and supports one side of the abdominal region, one side of the waist region or one side of the pelvis region of the body at the lower portion of the first support plate 210. For instance, when the brace 100 is worn, the second support plate may extend from the center of the front of the pelvis to the center of the rear of the pelvis.

In this case, like the first support plate 210, the inner surface of the second support plate 220 preferably comes into close contact with the surface of the body. Thus, the second support plate 220 is preferably configured to be curved so as to correspond to the curved shape of the surface of the body.

For instance, the second support plate 220 may include an extension part 221 curved and extended downward and outward from both ends of the second support plate, and an expansion part 222 the width of which is expanded and which is formed at the end of the extension part 221. The expansion part 222, which comes into close contact with the one side of the pelvis region of the body, is preferably configured to expand gradually from the end of the extension part 221 toward the center of the same so as not to loosen.

Meanwhile, the first and second support plates 210, 220 may be configured as a single plate consisting of metals, or synthetic resins such as soft plastics etc. Preferably, a plurality of plates consisting of different materials are piled in an up-down direction.

For instance, each of the first and second support plates 210, 220 may include a base plate 230 consisting of a soft material and having a shape corresponding to a curved shape of the surface of the body, and a reinforcement plate 240 coupled to the outer side of the base plate 230 and consisting of a synthetic resin.

In this case, the base plate 230 is preferably manufactured through 3D printing with a material like plastics, which have resilience and are bent and durable, such as polypropylene, polyurethane, Teflon, polyethylene etc. Further, preferably, parts of the base plate are separately printed so as to avoid the difficulty in manufacturing the base plate and to save the costs of manufacturing the same. In this case, a 3D model, manufactured on the basis of a measurement of a region of the body on which the brace 100 is worn, is used. Thus, the base plate 203 manufactured through 3D printing may come in to close and comfortable contact with the curved part of the surface of the body.

The reinforcement plate 240 is coupled to one surface of the base plate 230 so as to reinforce the strength of the brace 100. The reinforcement plate 240 may consist of a soft plastic such as polypropylene, poly Vinyl Chloride (PVC) etc. and may be integrally laser-cut using 3D modeling data. In this case, when being coupled to the base plate 230, the reinforcement plate 240 is preferably cut in the shape of a flat surface considering that the reinforcement plate will be curved in accordance with a curved part of the base plate 230.

Meanwhile, a shock absorbing member 250, which consists of an elastic material such as rubber, silicone or a sponge etc., may be coupled to the inner side of the base plate 230 so as to directly contact the body, thereby preventing the base plate from slipping and absorbing an external shock.

Further, a cover plate 260, which consists of a light metal such as aluminum etc., may be coupled to the outer side of the reinforcement plate 240. The cover plate 260 together with the reinforcement plate 240 reinforces the strength of the brace 100 and prevents damage such as a scratch etc. done to the reinforcement plate 240 and the base plate 230. In this case, preferably, the cover plate 260 is partially coupled to some sections such that the brace is lightened and reinforced. When necessary, the cover plate may be coupled along the entire length of the reinforcement plate 240.

A brace 100 according to the first embodiment of the present invention may further include a connecting member 400 coupled to one end of the first support plate 210 and one end of the second support plate 220 so as to connect the same, and a spine support member 500 coupled to the other end of the first support plate 210 and the other end of the second support plate 220 to connect the same. In this case, the connecting member 400 and the spine support member 500 may consist of metals or synthetic resins.

Herein, the connecting member 400 has the shape of a rectangular plate, and the upper end of the connecting member 400 is coupled to one end of the first support plate 210 while the lower end of the connecting member 400 is coupled to one end of the second support plate 220. The first and second plates 210, 220 may be coupled to the connecting member 400 with an engaging device such as a rivet, or a bolt etc., or through a coupling method such as adhesion, fusion or welding etc. When the brace 100 is worn, the connecting member 400 is positioned at the center of the abdominal region of the body.

Meanwhile, first coupling holes 410, spaced apart from each other in the widthwise direction thereof and extending in the lengthwise direction thereof, are formed at the connecting member 400 and penetrates the same. One end of the pressure band 300 that will be described hereunder is coupled to the connecting member 400 through the first coupling hole 410.

The spine support member 500 may have the shape of a rectangular plate, and have a curbed surface corresponding to the curved shape of the spine on the inner side of the spine support member 500 so as to comfortably support the spine region of the body, and a plurality of protrusion parts 510 that are spaced apart from each other along both edges of the spine support member in the widthwise direction thereof and protrude outward.

A second coupling hole 520 is formed at and passes through the center of the spine support member 500 in the lengthwise direction thereof, and the other end of the pressure band 300 that will be described hereunder is coupled to the spine support part 500 through the second coupling hole 520.

The connecting member 400 and the spine support member 500 are coupled to the support part 200 by an engaging device such as a rivet etc. The base plate 230, the reinforcement plate 240 and the shock absorbing member 250 and the cover plate 260 may be consecutively piled and may adhere to one another by means of an engaging device such as an adhesive material or a rivet. In this case, the connecting member 400, the spine support member 500 and the support part 200 may be integrally coupled by an engaging device such as a rivet etc. Additionally, the above-described shock absorbing member 250 is preferably added on the inner side the connecting member and the spine support member because the connecting member 400 and the spine support member 500 also closely contact the surface of the body.

The pressure band 300 connects the connecting member 400 and the spine support member 500 so as to face the support part 200 and may consist of an elastic material such as rubber or a synthetic fiber etc. Thus, when the brace 100 is worn, the support part 200 closely contacts one side of the abdominal region of the body while the pressure band 300 closely contacts the other side of the abdominal region of the body.

In this case, the connecting member 400 is positioned at the center of the abdomen at the front of the body, the spine support member 500 supports the spine region at the rear of the body, and the pressure band 300 goes from the connecting member 400, past the side and then is coupled to the spine support member 500 and pressurizes the side region in the direction of the spine so as to make a convex spine region normal.

A plurality of pressure bands 300 may be spaced apart from each other and connected to each other along the lengthwise directions of the connecting member 400 and the spine support member 500. The number, width, length etc. of the pressure bands 300 may be selected according to users' needs.

Users may adjust the length of the pressure band 300 according to their body size and the degree of curvature of their spine so as to adjust the intensity of pressure applied to a curved region of their spine.

As an example, one end of the pressure band 300 is coupled to the connecting member 400 (or spine support member 500) while the other end penetrates the spine support member 500 (or connecting member 400) such that a first coupling member 310 at the end of the pressure band 300 may be coupled to a second coupling member 320 at one side of the pressure band 300 so as to correspond to the same. In this case, the first and second coupling members 310, 320 may consist of an engaging device such as a hook and loop tape (Velcrom) or a snap button etc., which is attachable and detachable. Users adjust the length of the pressure band 300 by pulling the pressure band and then couple and fix the first and second coupling members 310, 320 to each other such that the side of their body is continuously pressurized by the pressure band 300.

As another example, the pressure band 300 may include a first band (invisible) whose one end is coupled to the connecting member 400 and whose other end is provided with a first coupling member 310, and a second band (invisible) whose one end is provided with a second coupling member 320 corresponding and coupled to the first coupling member 310 and whose other end is coupled to the spine support member 500. Further, though not illustrated in the drawings, a length adjusting device (invisible), which is usually used for adjusting the length of the strap of a bag or a backpack, may be provided on one side of the pressure band 300.

A brace 100 according to the first embodiment of the present invention may further include a fixing band 600 that is supported by the second support plate 220 of the support part 200 and covers the thigh of the body. Herein, the fixing band 600 prevents the movement such as an upward crawl of the support part 200 during physical activities.

To this end, a loop member 270 is configured to protrude downward from one side of the second support plate 220, and the fixing band 600 penetrating the loop member 270 covers the thigh of the body and is fixed. The upper end of the loop member 270 is coupled to one side of the second support plate 220 through adhesion, fusion or sewing etc. and is preferably coupled to one side of the second support plate 220 by means of an engaging device such as a rivet etc.

The fixing band 600 may consist of an elastic material such as fabric, leather, a synthetic resin or rubber or synthetic fiber etc. and may be configured to have the shape of a ring with elasticity. Further, the fixing band may be configured to have the shape of a length adjustable strap. In this case, coupling members the same as the first and second coupling members 310, 320 may be provided on one side and the other side of the strap.

Figure 5:
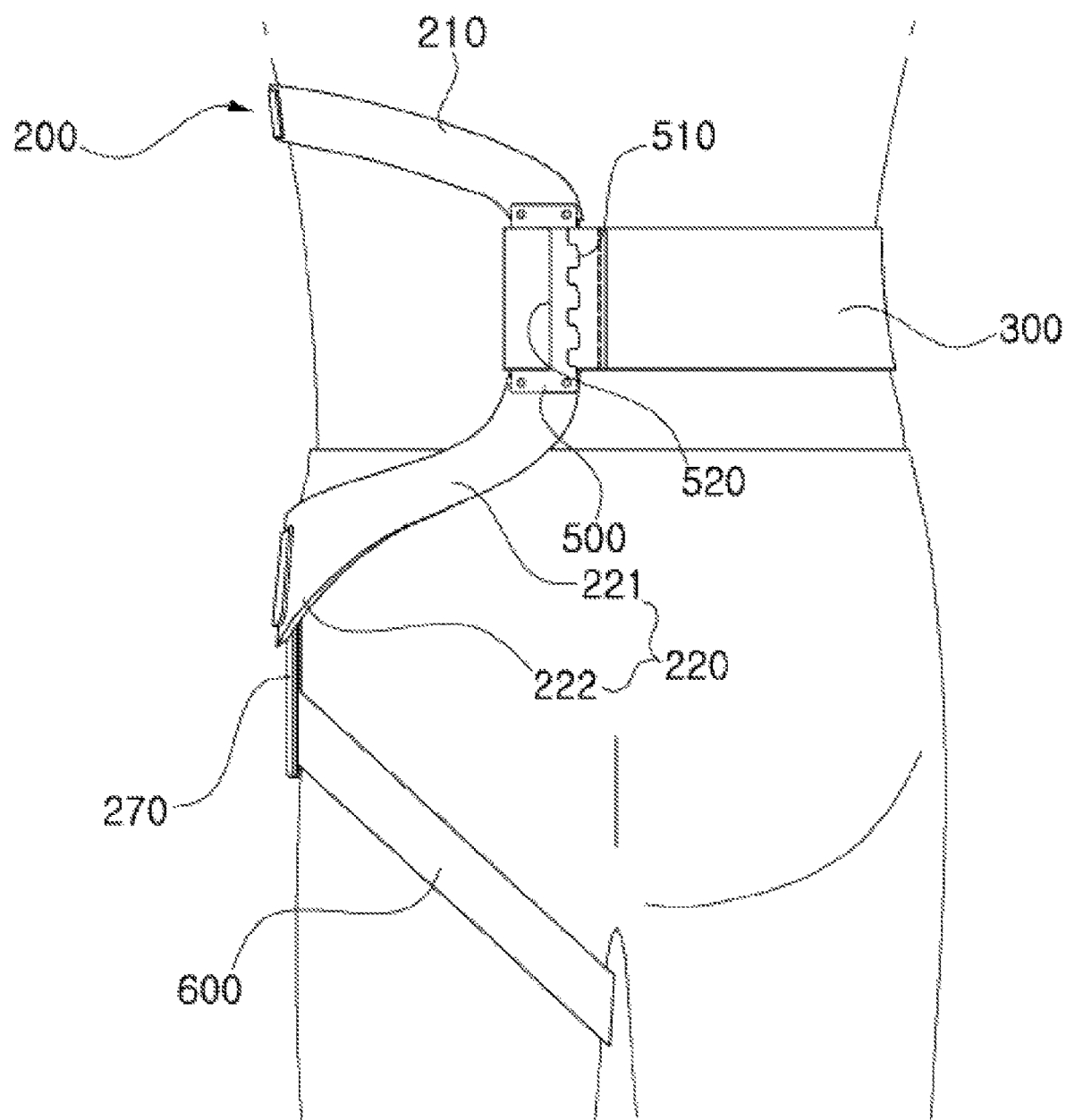
FIGS. 5 and 6 are views illustrating a state where a scoliosis brace according to the first embodiment of the present invention is being used.
Figure 6:
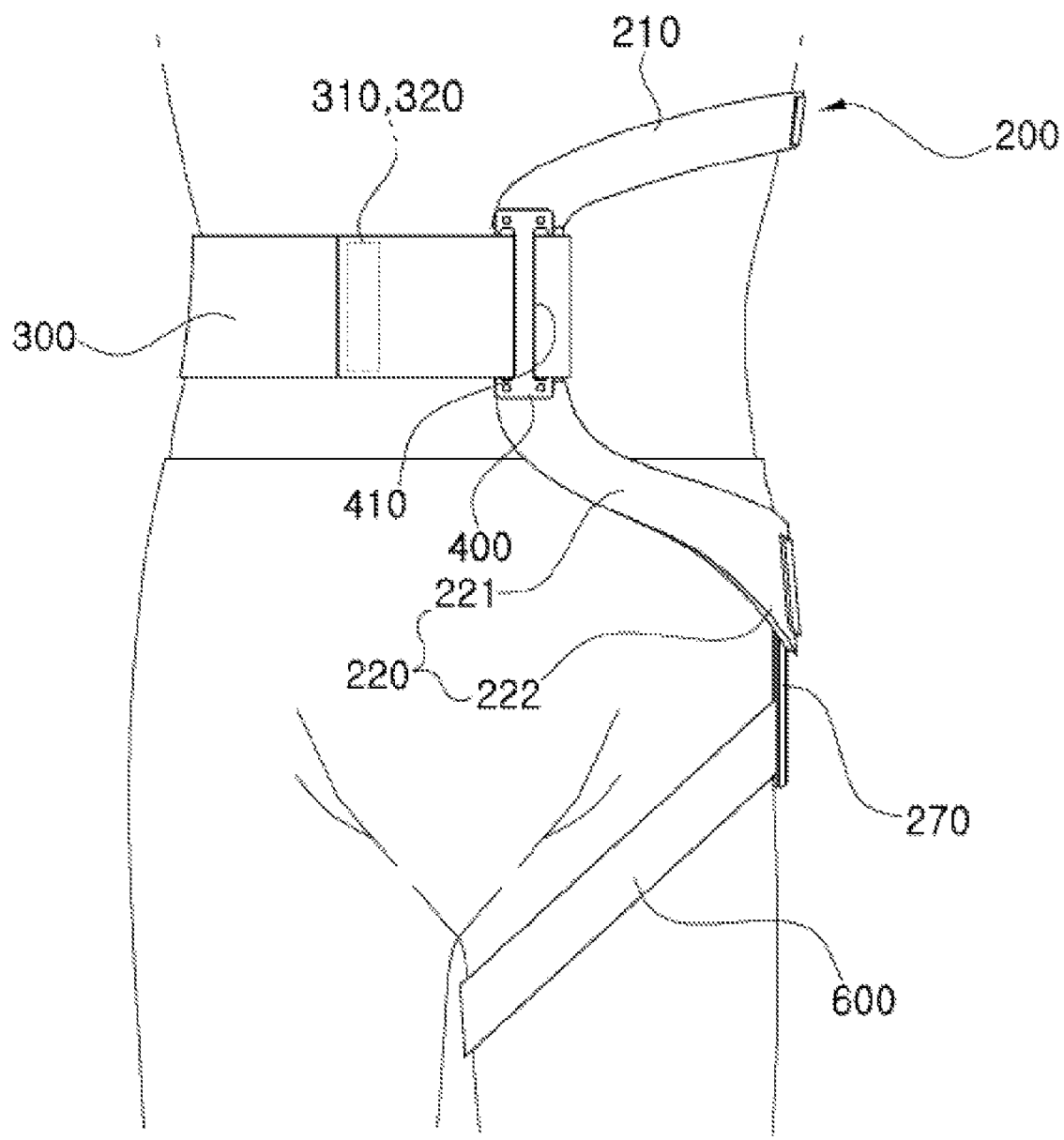

FIGS. 5 and 6 are views illustrating a state where a scoliosis brace according to the first embodiment of the present invention is being used.

When a brace 100 according to the first embodiment of the present invention is worn, the support part 200 is positioned on one side of the abdominal region of the body, the pressure band 300 is tightened and fixed so as to pressurize the other side of the abdominal region of the body, and then the fixing band 600 is worn on the thigh region. However, the above-described method for wearing a brace is applied only to the first embodiment of the present invention. Certainly, the order of wearing a brace may be changed if necessary.

Figure 7:
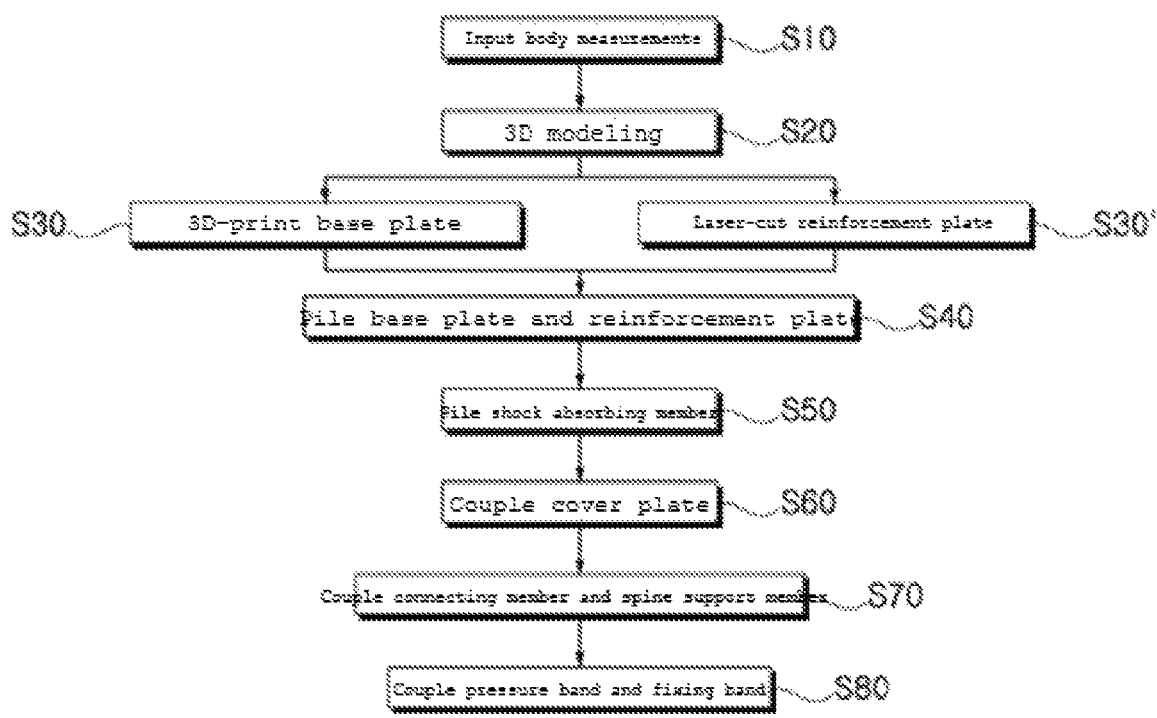
FIG. 7 is a flow chart of a method for manufacturing a scoliosis brace according to the first embodiment of the present invention.

FIG. 7 is a flow chart of a method for manufacturing a scoliosis brace according to the first embodiment of the present invention.

Below, each manufacturing step for a brace according to the first embodiment of the present invention will be described with reference to FIG. 7.

Step of Measuring the Body and Inputting the Same (S10):

Measurements of body parts (area under the chest, the waist, the pelvis etc.) of a user who is going to wear a brace 100 are taken and the measurements are input. However, if there are measurements that were taken previously and there is no change in the measurements, the measurements may be used.

Step of 3D Modeling (S20):

Three-dimensional modeling with respect to the body parts are performed on the basis of the input measurements with a computer. In this case, data in which the brace 100 is virtually worn on an embodied 3D model may be transmitted to the user and then confirmed by the user when necessary.

Step of 3D-Printing a Base Plate (S30):

A base plate 230 is 3D-printed in accordance with the 3D modeling. Robust plastics (ABS, PLA etc.), flexible synthetic resins such as polypropylene, polyurethane, Teflon, polyethylene etc., and a combination thereof may be used as a material that will be piled in 3D printing.

In this case, the base plate 230 may be entirely printed out at a time. However, considering the base plate 230 is formed as a curved 3D shape, layers of flat shapes are piled one by one so as to form a 3D shape. In this process, a plurality of supporters (invisible) have to be separately manufactured to support the 3D shape. Additionally, after the base plate 230 is manufactured, the supporters integrally formed in the 3D shape have to be removed.

A method for manufacturing a brace 100 according to the first embodiment of the present invention includes dividing the base plate 230 into a plurality of parts such that the base plate may be formed even without separate supporters, and divisionally printing out each part.

The ends of the divisionally printed parts may adhere to each other or are welded to each other and may be coupled to one surface of a reinforcement plate 240 by an engaging device such as a rivet etc., so as to form a base plate 230.

Step of Laser-Cutting a Reinforcement Plate (S30'):

A reinforcement plate 240 is integrally laser-cut on the basis of 3D modeling data. In this case, the reinforcement plate 240 is cut from a flat plate consisting of a flexible synthetic resin material such as polypropylene, PVC etc. Thus, both surfaces of the reinforcement plate 240 are formed to be flat.

Then the reinforcement plate 240 comes into close contact with the base plate 230 along the curved surface of the base plate 230. In this case, when being laser-cut, the reinforcement plate 240 is preferably cut in the shape of a flat surface considering the 3D shape of the base plate 230 so as not to escape from the region of the base plate 230, not to be corrugated and not to be overlapped. That is, a flat surface shape is drawn from 3D modeling data and then a reinforcement plate 240 is laser-cut in accordance with the shape.

Step of Piling a Reinforcement Plate (S40):

In the step of forming a reinforcement plate (S30'), the reinforcement plate 240 having been laser-cut in the shape of a flat surface is piled on the outer surface of the base plate 230 curved in a 3D shape. In this case, an adhesive material may be used to attach the reinforcement plate.

Step of Piling a Shock Absorbing Member (S50):

A shock absorbing member 250, which consists of an elastic material such as rubber, silicone or a sponge etc., is piled on the inner surface of the base plate 230. In this case, as in the step of forming a reinforcement plate (S30'), the shock absorbing member 250 may be laser-cut in the shape of a flat surface considering the 3D shape of the base plate 230 and may be attached with an adhesive material. Further, the step of piling a shock absorbing member (S50) may be performed before the step of piling a reinforcement plate (S40).

Step of Coupling a Cover Plate (S60):

A cover plate 260, which consists of a light metal such as aluminum etc., is piled on the outer surface of the reinforcement plate 240. In this case, as in the step of forming a reinforcement plate (S30'), the cover plate 260 may be cut or laser-cut in the shape of a flat surface considering the 3D shape of the base plate 230. Further, the cover plate 260 may be formed so as to correspond to the entire shape or some sections of the reinforcement plate 240.

The cover plate 260 is coupled to the outer surface of the reinforcement plate 240 by means of an adhesive material and preferably, is integrally coupled to the base plate 230, the reinforcement plate 240, the shock absorbing member 250 and the cover plate 260 by means of an engaging device such as a rivet etc. In this case, the cover plate 260 is preferably coupled to some sections of the reinforcement plate 240, and when necessary, may be coupled to the reinforcement plate along the entire length of the reinforcement plate 240.

After the step of coupling a cover plate (S60), first and second support plates 210, 220 are prepared. In this case, a loop member 270 consisting of fabric, leather or a synthetic resin, a synthetic fiber is coupled to one side of the second support plate 220 by means of an engaging device such as a rivet etc. However, the coupling of the loop member 270 may also be performed after the step of coupling a connecting member and a spine support member (S70).

Step of Coupling a Connecting Member and a Spine Support Member (S70):

A connecting member 400 and a spine support member 500 separately manufactured are respectively coupled to both ends of the first and second support plates 210, 220 manufactured through the step of coupling a cover plate (S60) by means of an engaging device such as a rivet.

Meanwhile, this step may be performed before the step of piling a shock absorbing member (S50). That is, the step of coupling a connecting member and a spine support member (S70) in which a connecting member 400 and a spine support member 500 are coupled to a support plate 200 is performed, and then the step of piling a shock absorbing member (S50) may be performed such that the shock absorbing member 250 is attached to the inner side of the connecting member 400 and the spine support member 500.

Step of Coupling a Pressure Band and a Fixing Band (S80):

A pressure band 300 is coupled to one side of the support part 200. As an example, one end of the pressure band 300 is allowed to pass through a second coupling hole 520 of the spine support member 500 and then is sewn and fixed. In this case, when the brace is being used, the other end of the pressure band 300 is allowed to pass through a first coupling hole 410 of the connecting member 400 and is tightened so as to adjust length thereof, and then first and second coupling members 310, 320 are coupled to each other and fixed.

As another example, a pair of pressure bands are prepared. The end of any one of the pressure bands is allowed to pass through a first coupling hole 410 of the connecting member 400 and then sewn and fixed. In this case, the end of the rest pressure bands is allowed to pass through a second coupling hole 520 of the spine support member 500 and then sewn and fixed.

A fixing band 600 is inserted so as to penetrate the loop member 270, and when necessary, one side of the fixing band 600 may be coupled to one side of the loop member 270 by means of sewing, adhesion, or fusion, or an engaging device such as a rivet etc.

Unlike conventional methods for manufacturing a brace in which casts are needed, the above-described manufacturing method for a brace helps save time and effort in manufacturing a brace.

Additionally, a base plate 230 is manufactured using 3D modeling on the basis of measurements of the body. Thus, a support part 200 of the brace 100 closely contacts a curved surface of the body thereby causing no inconvenience to users during physical activities and making the brace comfortable to wear.

Additionally, in case where a brace 100 has to be re-manufactured due to damage done to the brace 100 etc., as long as measurements of the body or 3D modeling data of a user are stored, the body of the user does not have to be measured again.

Further, according to the above-described manufacturing method for a brace, it is unnecessary for users to deliver a cast to a company that manufactures a brace 100 and to visit the company to make a cast. All users have to do is measure their bodies and deliver the measurements or 3D modeling date to a company that manufactures a brace. Thus, a brace may be customized in remote places.

Figure 8:
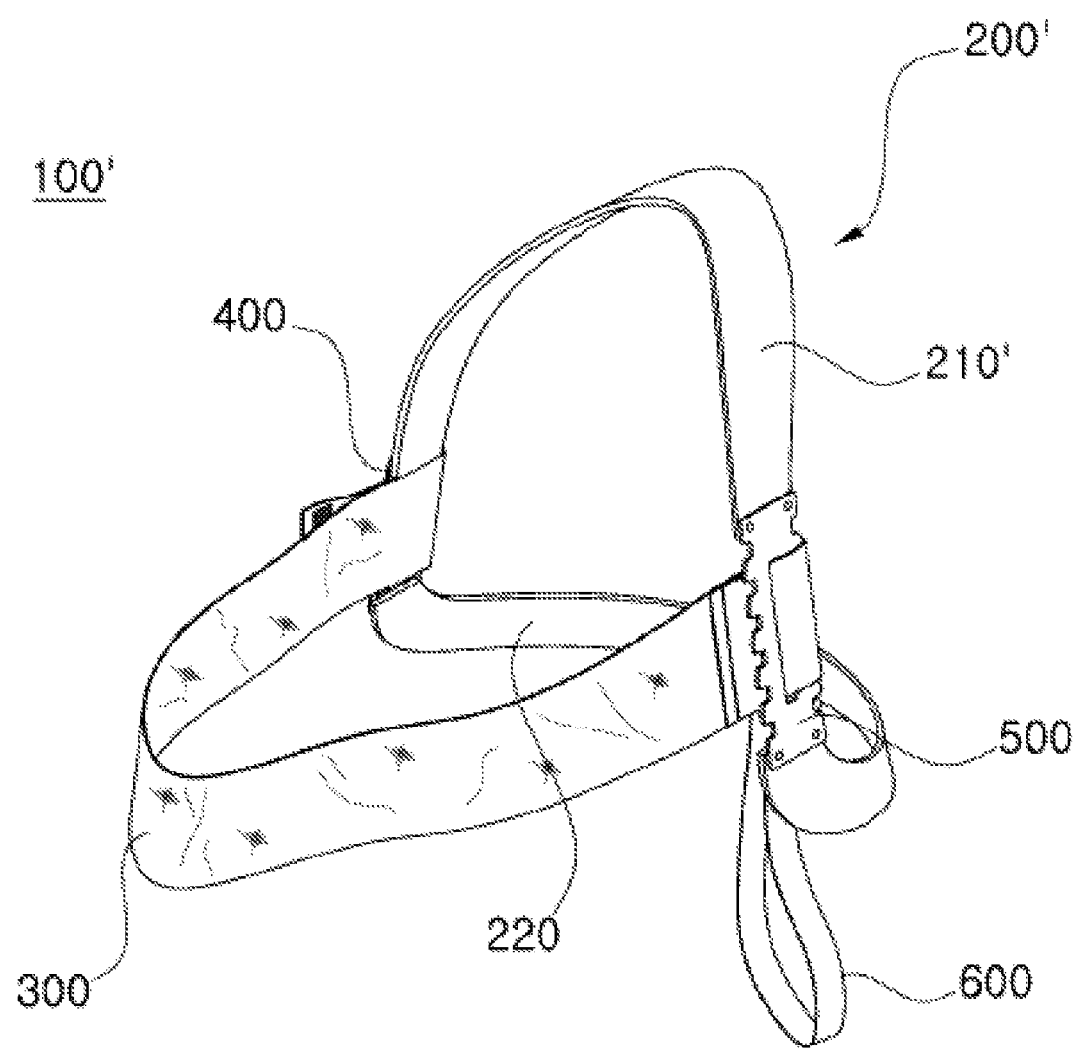
FIG. 8 is a perspective view of a scoliosis brace according to the second embodiment of the present invention.

FIG. 8 is a perspective view of a scoliosis brace according to the second embodiment of the present invention, and FIG.

9 is a view illustrating a state where a scoliosis brace according to the second embodiment of the present invention is being used.

A configuration of a scoliosis brace 100' according to the second embodiment of the present invention and a manufacturing method therefor are similar to those of a scoliosis brace 100 according to the first embodiment that has been described, except for a first support plate 210', constituting a support part 200', which is configured to be hung on one shoulder of the body. Thus, like reference numerals are given to the components that perform functions the same as those of the components of the first embodiment that has been described, and description of such components will be omitted.

Figure 9:
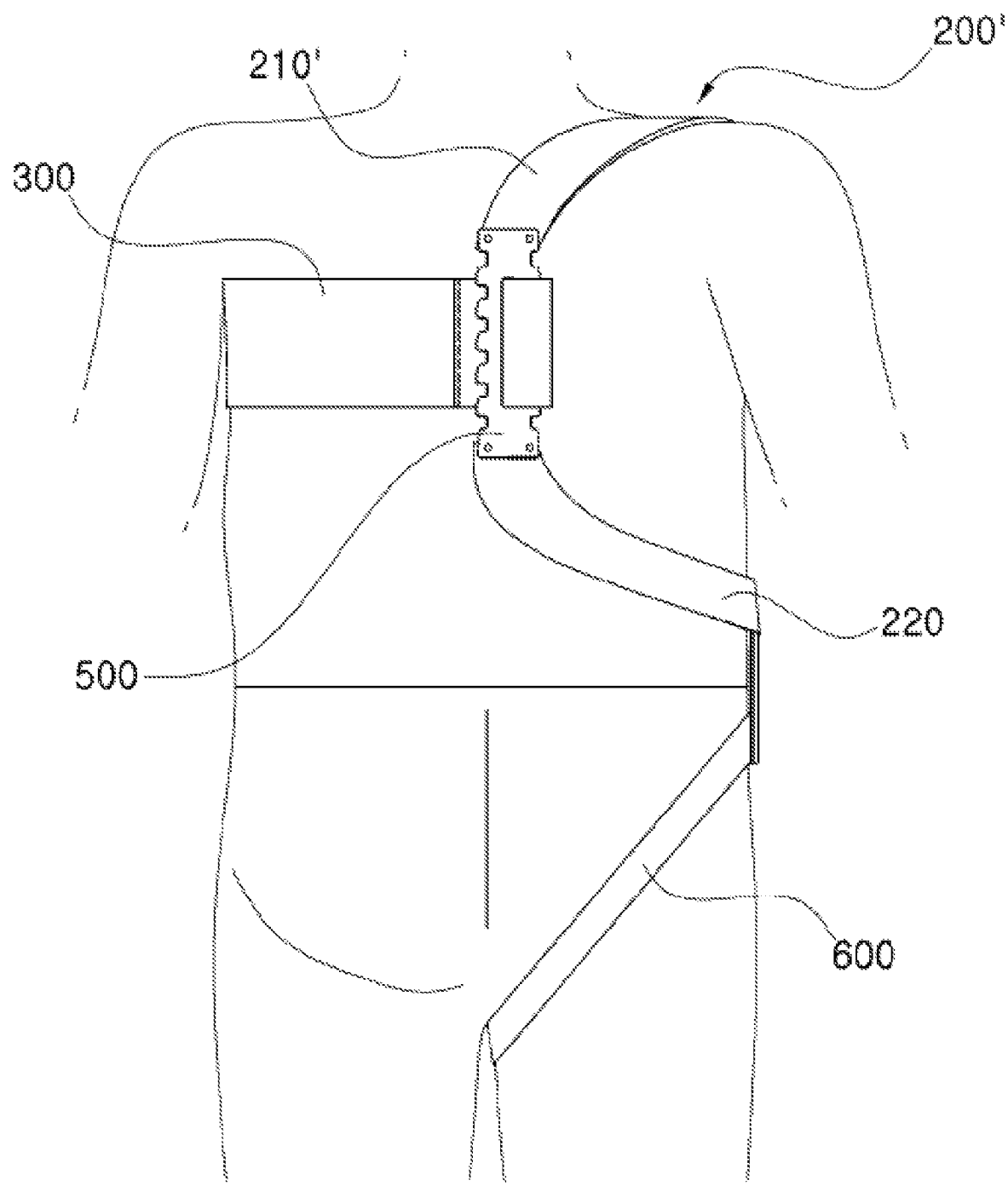
FIG. 9 is a view illustrating a state where a scoliosis brace according to the second embodiment of the present invention is being used.

FIG. 9 is a view illustrating the rear of the body on which a scoliosis brace 100' according to the second embodiment of the present invention is worn. The middle portion of a first support plate 210' is hung on the right shoulder, and both ends of the first support plate are configured to curvedly extend so as to respectively come into close contact with the center of the chest and back regions. In this case, a second support plate 220 closely contacts the waist region, the abdominal region, or the pelvis region on the right side of the body, and a pressure band 300 is connected between a connecting member 400 and a spine support member 500 so as to pressurize the chest region or the abdominal region on the left side of the body.

Herein, certainly, the loop member 270 and the fixing band 600 of the first embodiment that has been described may be formed on one side of the second support plate 220 when necessary, and the support part 200' and the pressure band 300 may be worn on the opposite of what has been described above. For instance, the support part 200' may be worn on the left side of the body while the pressure band 300 may be worn on the right side of the body.

Figure 10:
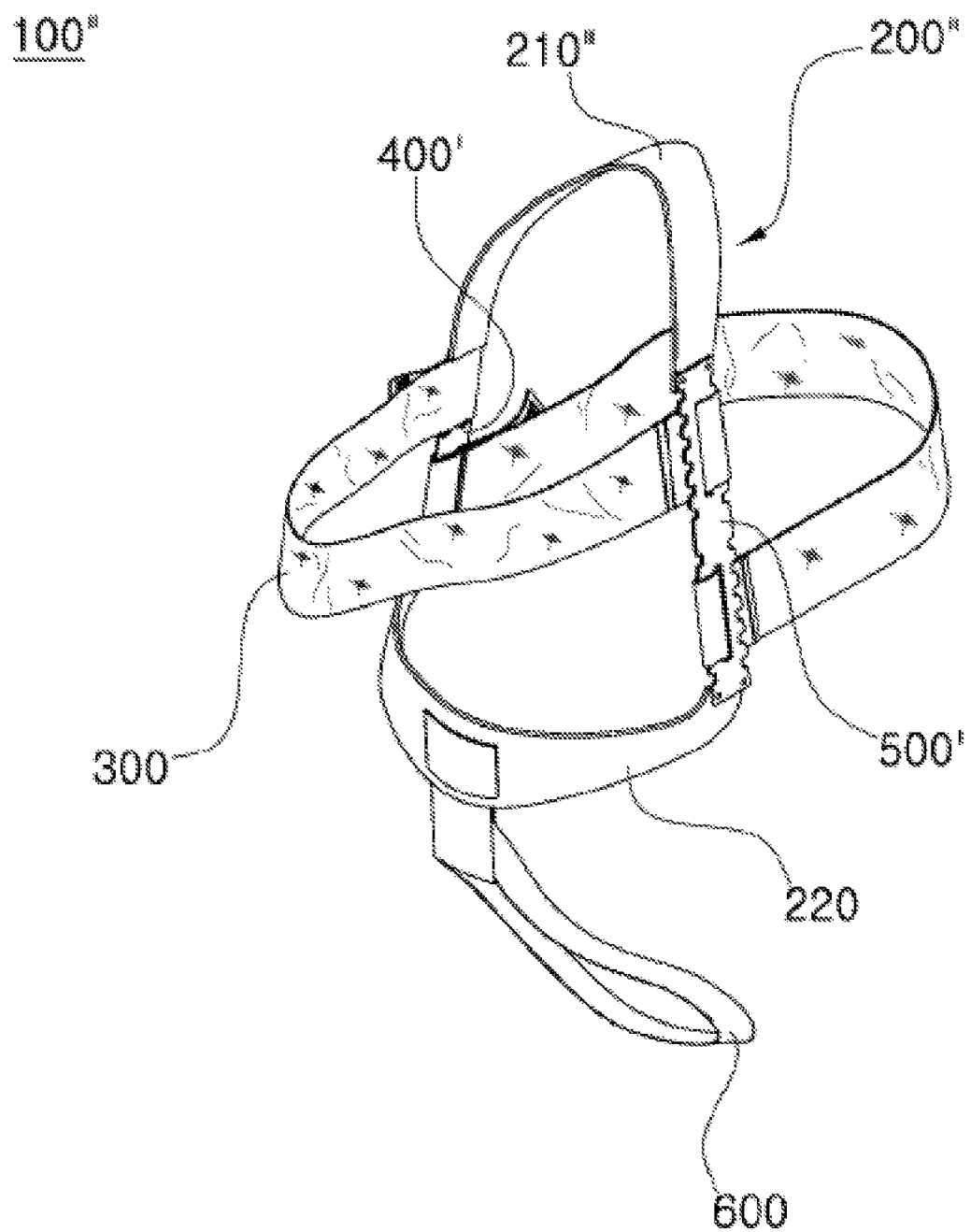
FIG. 10 is a perspective view of a scoliosis brace according to the third embodiment of the present invention.
Figure 11:
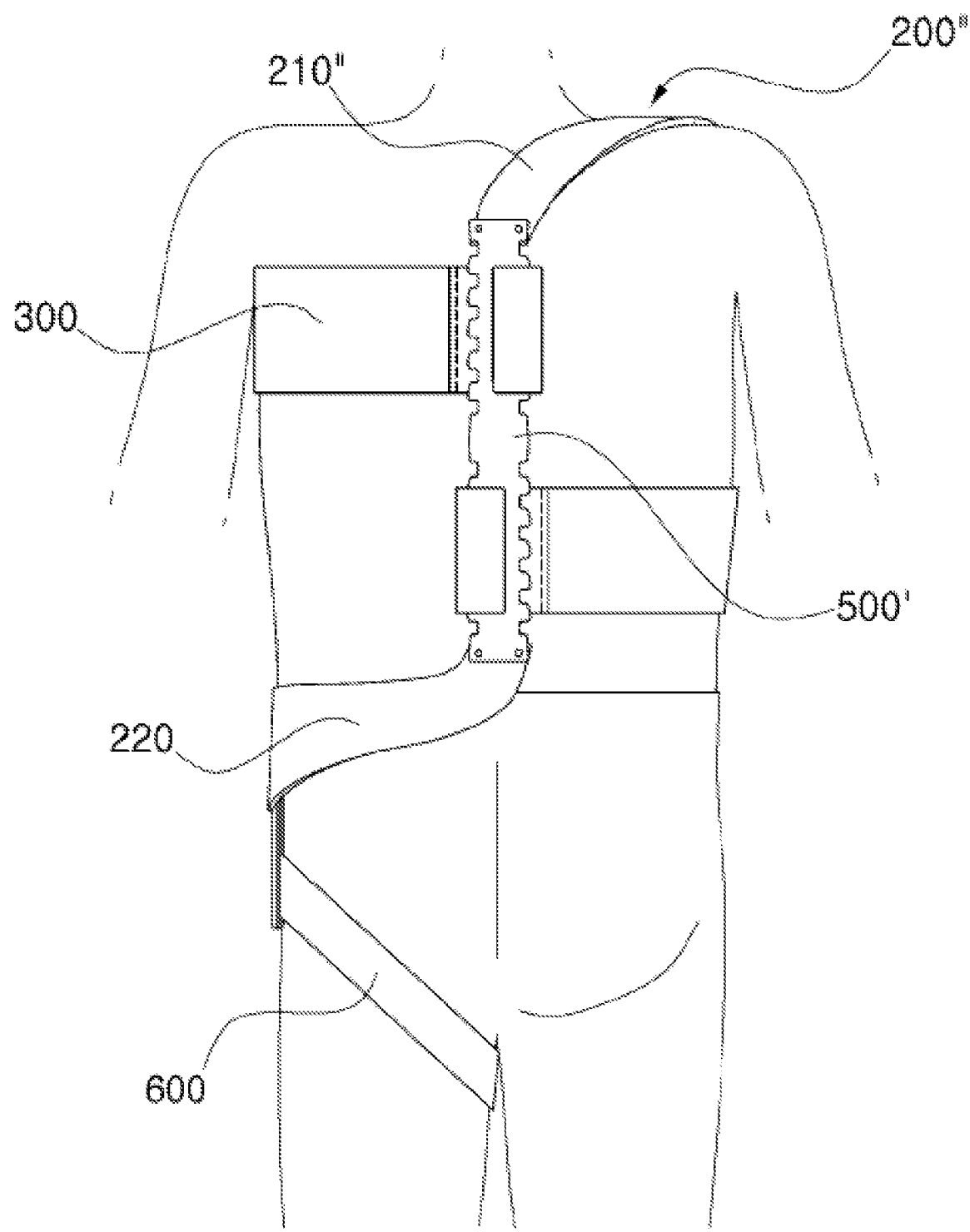
FIG. 11 is a view illustrating a state where a scoliosis brace according to the third embodiment of the present invention is being used.

FIG. 10 is a perspective view of a scoliosis brace according to the third embodiment of the present invention, and FIG. 11 is a view illustrating a state where a scoliosis brace according to the third embodiment of the present invention is being used.

A configuration of a scoliosis brace 100" according to the third embodiment of the present invention and a manufacturing method therefor are similar to those of a scoliosis brace 100 according to the first embodiment that has been described, except for a first support plate 210", constituting a support part 200", which is configured to be hung on one shoulder of the body, and a pair of pressure bands 300 which extend in the direction in which the pair of pressure bands are opposite to each other and are spaced apart from each other. Thus, like reference numerals are given to the components that perform functions the same as those of the components of the first embodiment that has been described, and description of such components will be omitted.

FIG. 11 is a view illustrating the rear of the body on which a scoliosis brace 100" according to the third embodiment of the present invention is worn. The middle portion of a first support plate 210" is hung on the right shoulder, and both ends of the first support plate are configured to curvedly extend so as to respectively come into close contact with the center of the chest and back regions. In this case, a second support plate 220 closely contacts the waist region, the abdominal region, or the pelvis region on the left side of the body.

A pair of pressure bands 300 are connected between a connecting member 400' and a spine support member 500' such that the upper pressure band 300 pressurizes the chest region or the abdominal region on the left side of the body while the lower pressure band 300 pressurizes the abdominal region or the waist region on the right side of the body.

Herein, certainly, the loop member 270 and the fixing band 600 of the first embodiment that has been described may be formed on one side of the second support plate 220 when necessary, and the support part 200" and the pressure band 300 may be worn on the opposite of what has been described above. For instance, the support part 200" may be worn such that the first support plate 210" is hung on the left shoulder. In this case, the upper pressure band 300 pressurizes the chest region or the abdominal region on the right side of the body while the lower pressure band 300 pressurizes the abdominal region or the waist region on the left side of the body.

Meanwhile, preferably, a pair of first coupling holes 410 and a pair of second coupling holes 520 respectively penetrate and are formed on the connecting member 400' and the spine support member 500' so as to be spaced apart from each other such that the pair of pressure bands 300 may be spaced apart from each other and connected to each other between the connecting member 400' and the spine support member 500'.

The embodiments of the present invention have been described. However, it should be understood that the present invention may be modified in various forms by one of ordinary skill in the art to which the present invention pertains within the scope of the appended claims of the present invention.

The invention claimed is:

1. A scoliosis brace comprising:
a support part, that is c-shaped, worn to cover on only one side of an abdominal region or only one side of a shoulder region of a body; and
a pressure band consisting of an elastic material,
wherein one end of the pressure band is connected to one side of the support part, then the pressure band is wrapped around either only a front and back of an abdominal region of the body or a chest region of the body to pressurize and support thereto, and other end of the pressure band is connected to other side of the support part,
wherein a length of the pressure band is adjustable and the one end of the pressure band comprises a pair of coupling members to be attached or detached to the support part.

2. The scoliosis brace according to claim 1,
wherein the support part comprises a first support plate covering one side of the abdominal region of the body to support thereto, and a second support plate spaced apart from a lower portion of the first support plate and covering one side of the abdominal region, one side of a waist region, or one side of a pelvis region of the body so as to support thereto.

3. The scoliosis brace according to claim 2,
wherein the second support plate comprises an extension part curved and extended downward and outward from both ends of the second support plate, and a width of an expansion part is expanded, and formed at an end of the extension part.

4. The scoliosis brace according to claim 2,
wherein the support part further comprises a connecting member whose upper end is coupled to one end of the first support plate and whose lower end is coupled to one end of the second support plate, and a spine support member whose upper end is coupled to other end of the first support plate, whose lower end is coupled to other end of the second support plate, and which supports a spine region of the body.

5. The scoliosis brace according to claim 4,
wherein the support part further comprises a first coupling hole formed at a connecting member and coupled to one end of the pressure band, and a second coupling hole formed at the spine support member and coupled to other end of the pressure band.

6. The scoliosis brace according to claim 2,
wherein the support part further comprises a loop member protruding downward from one side of the second support plate, and a fixing band penetrating the loop member and covering a thigh region of the body.

7. The scoliosis brace according to claim 1,
wherein the support part comprises a base plate consisting of a soft material and having a shape corresponding to a curved shape of a surface of the body, and a reinforcement plate consisting of a synthetic resin and coupled to an outer side of a base plate.

8. The scoliosis brace according to claim 7,
wherein the support part further comprises a shock absorbing member consisting of an elastic member and coupled to an inner side of the base plate.

9. The scoliosis brace according to claim 8,
wherein the support part further comprises a cover plate consisting of a metallic material and coupled to the outer side of the reinforcement plate.

10. The scoliosis brace according to claim 8,
wherein the base plate comprises a plurality of parts that are divisionally printed out through 3D printing.

11. The scoliosis brace according to claim 10,
wherein the reinforcement plate is integrally formed through laser cutting.

12. A manufacturing method for a scoliosis brace, comprising:
(a) taking measurements of a user's body and inputting measurement;
(b) performing 3D modeling on the basis of the measurement;
(c) 3D-printing a base plate according to a shape of a 3D model;
(d) piling a reinforcement plate on an outer surface of the base plate;
(e) adding a shock absorbing member on an inner surface of the base plate; and
(f) setting a length of the pressure band is adjustable and the pressure band comprises a pair of coupling members provided on one side thereof;
(g) coupling a cover plate to the outer surface of the reinforcement plate.

13. The manufacturing method for a scoliosis brace according to claim 12,
wherein the (c) step comprises printing out a plurality of parts divisionally through 3D printing.

14. The manufacturing method for a scoliosis brace according to claim 13,
wherein the (d) step comprises laser-cutting a reinforcement plate consisting of a synthetic resin integrally.

\* \* \* \* \*